(12) United States Patent
Bettermann et al.

(10) Patent No.: US 9,030,665 B2
(45) Date of Patent: May 12, 2015

(54) METHOD FOR MONITORING AND/OR REGULATING FUEL CELLS

(75) Inventors: Hans Bettermann, Neuss (DE); Peter Fischer, Duesseldorf (DE); Arno Goedecke Reichelt, Duesseldorf (DE); Irmgard Buder, Duisburg (DE); Volker Peinecke, Muelheim-Ruhr (DE)

(73) Assignee: Heinrich-Heine Universität Düsseldorf (DE)

( * ) Notice: Subject to any disclaimer, the term of this patent is extended or adjusted under 35 U.S.C. 154(b) by 31 days.

(21) Appl. No.: 13/512,602

(22) PCT Filed: Dec. 6, 2010

(86) PCT No.: PCT/EP2010/068941
§ 371 (c)(1),
(2), (4) Date: May 30, 2012

(87) PCT Pub. No.: WO2011/069948
PCT Pub. Date: Jun. 16, 2011

(65) Prior Publication Data
US 2012/0236311 A1    Sep. 20, 2012

(30) Foreign Application Priority Data
Dec. 8, 2009 (DE) .......................... 10 2009 057 130

(51) Int. Cl.
| G01N 21/59 | (2006.01) |
| H01M 8/04 | (2006.01) |
| G01N 21/67 | (2006.01) |

(52) U.S. Cl.
CPC ........... *H01M 8/04447* (2013.01); *G01N 21/67* (2013.01); *H01M 8/04089* (2013.01); *H01M 8/04455* (2013.01); *Y02E 60/50* (2013.01)

(58) Field of Classification Search
CPC ... Y02E 60/50; Y02T 90/32; H01M 8/04402; H01M 8/0441; H01M 8/04462; G01N 27/419; G01N 21/05; G01N 2291/0215
USPC .......... 356/432–440; 429/19, 24, 25, 30, 415, 429/429
See application file for complete search history.

(56) References Cited

U.S. PATENT DOCUMENTS

| 3,292,988 A | 12/1966 | Kimball |
| 3,458,258 A | 7/1969 | Krugers |

(Continued)

FOREIGN PATENT DOCUMENTS

| DE | 423436 | 12/1925 |
| DE | 3623044 | 2/1987 |

(Continued)

OTHER PUBLICATIONS

International Search Report; PCT/EP2010/068941; Heinrich Heine Universitaet Duesseldorf; Int'l File Date: Dec. 6, 2010; 3 pgs.

*Primary Examiner* — Hoa Pham
(74) *Attorney, Agent, or Firm* — Schmeiser, Olsen & Watts, LLP

(57) ABSTRACT

The invention relates to a method for monitoring and/or regulating fuel cells, in particular comprising determining the composition of the operating gases of the fuel cells. The method comprises the following steps: introducing the gas mixture to be analyzed into a measuring cell (1); producing an arc in the measuring cell (1); absorbing the radiation emitted by the arc; optical filtering of the emitted radiation and/or spectral decomposition of the emitted radiation; converting the emitted radiation into an electric signal; evaluating the electric signal.

21 Claims, 5 Drawing Sheets

(56) References Cited

U.S. PATENT DOCUMENTS

| | | | |
|---|---|---|---|
| 3,508,106 | A | 4/1970 | Vecsernyes |
| 3,545,863 | A | 12/1970 | Ault et al. |
| 3,791,743 | A | 2/1974 | Cody et al. |
| 4,723,438 | A | 2/1988 | Adler-Golden |
| 4,801,209 | A | 1/1989 | Wadlow |
| 5,168,323 | A | 12/1992 | Purtschert et al. |
| 5,570,179 | A | 10/1996 | Weckstroem |
| 5,920,400 | A | 7/1999 | Eisemann et al. |
| 6,011,882 | A * | 1/2000 | Dasgupta et al. ............... 385/12 |
| 6,034,768 | A | 3/2000 | Fraser et al. |
| 6,043,881 | A | 3/2000 | Wegrzyn et al. |
| 6,381,014 | B1 | 4/2002 | Platzer |
| 6,623,976 | B1 | 9/2003 | Hale et al. |
| 6,842,705 | B2 * | 1/2005 | Moriyama ..................... 702/45 |
| 7,326,926 | B2 * | 2/2008 | Wang ........................... 250/288 |
| 8,040,517 | B1 * | 10/2011 | Wu et al. ..................... 356/432 |
| 2002/0017124 | A1 * | 2/2002 | Dempster et al. ............. 73/23.2 |
| 2002/0140932 | A1 * | 10/2002 | Satou et al. .................. 356/311 |
| 2002/0177017 | A1 * | 11/2002 | Nelson et al. .................... 429/22 |
| 2006/0147765 | A1 * | 7/2006 | Barrett ............................ 429/13 |
| 2007/0148510 | A1 * | 6/2007 | Milacic ........................... 429/22 |
| 2009/0047553 | A1 | 2/2009 | Kizaki |
| 2009/0132206 | A1 | 5/2009 | Gamache et al. |
| 2009/0145778 | A1 * | 6/2009 | Allmendinger ............... 205/789 |
| 2009/0272896 | A1 * | 11/2009 | Belyakov et al. ............. 250/286 |
| 2012/0064422 | A1 * | 3/2012 | Takeuchi et al. ............. 429/423 |
| 2012/0189876 | A1 * | 7/2012 | Fabian et al. ..................... 429/9 |
| 2012/0270127 | A1 * | 10/2012 | Paganelli ...................... 429/429 |

FOREIGN PATENT DOCUMENTS

| | | |
|---|---|---|
| DE | 4113404 | 10/1992 |
| DE | 102006001778 | 7/2007 |
| GB | 727410 | 3/1955 |
| GB | 873576 | 7/1961 |
| GB | 1201005 | 8/1970 |
| WO | 2006020702 | 2/2006 |
| WO | 2007012904 | 2/2007 |

* cited by examiner

METHOD FOR MONITORING AND/OR REGULATING FUEL CELLS

FIELD OF TECHNOLOGY

The following relates to a method for monitoring and/or regulating fuel cells, comprising determining the composition of operating gases of fuel cells.

BACKGROUND

Today, highly efficient energy conversion systems based on fuel cells are the focus of global research and development activities, because compared to systems based on conventional energy sources they show considerable advantages with regards to efficiency and exhaust emissions. In addition to the construction of stationary power plants, their greatest potential is in automotive construction.

The effective principle of PEM (Polymer Electrolyte Membrane) fuel cells is based on a controlled electrochemical reaction of hydrogen and oxygen utilizing the electric energy emitted. These fuel cells comprise an anode chamber and a cathode chamber, separated by an electrolyte membrane. At the anode side of the membrane, hydrogen molecules are catalytically split and move in the form of protons into the cathode chamber, where they form water with the oxygen ions. This way, fuel cells generate electrochemical energy. Preferably air may serve as the oxygen supplier at the cathode side, which allows a particularly economic operation.

However, in air-operated PEM-fuel cells a problem arises, for example caused by aging, and the gas permeability of the membrane accompanied here due to the increased permeation of nitrogen from the air into the anode chamber. This is visible by the accumulation of nitrogen at the side of the anode. A critical situation develops when micro-fractures form in the membrane, for example macroscopic cracks. In case of a macroscopic crack of the membrane overheating occurs, due to direct catalytic incineration of hydrogen at the leakage site, which directly leads to the destruction of the membrane and thus to the fuel cell failing to function.

Furthermore, another type of malfunction is possible, which may occur by abnormal concentrations of water vapors of the anode gas. The transportation of ions through the PEM is only possible with sufficient moisture. Dehydration due to insufficient concentration of water vapors of the supply gas leads under load to a local increase of the current density in the still sufficiently moistened membrane areas, and thus may also lead to damages up to a failure of the fuel cell due to overload. Therefore it is important for the operation of air-operated PEM-fuel cells to reliably prove small amounts of nitrogen in the anode chamber, in addition to various concentrations of water vapor. This way, on the one hand a current permeability of the membrane can be monitored, which allows conclusions about the aging process of the membrane and thus leakages connected thereto. On the other hand it is possible to monitor the current moisture level. This way the fuel cell processes can be reliably controlled and the life of the fuel cell is increased, which increases the maintenance intervals required.

A method to measure nitrogen in a gas is known from DE 602 23 961 T2, in which trace amounts of nitrogen in krypton or xenon gas are measured using a gas discharge tube in a semiconductor-production process. The intensity of the light generated by the discharge in the gas discharge tube is measured via a spectrophotometer. Here, the underlying gas is restricted to noble gases, such as krypton and xenon.

A sensor is known from U.S. Pat. No. 5,570,179 for the spectroscopic analysis of gaseous mixtures. This sensor operates with a silent electric discharge. This silent electric discharge could not be maintained in a typical gas pressure of approximately one bar, thus the system is not suitable for use in fuel cell systems.

U.S. Pat. No. 5,168,323 describes a device for determining contaminants in gases. This device is particularly used for determining contaminants in noble gases, such as helium. Here, no indication is given for the determination of nitrogen concentrations in an atmosphere similar to the one of fuel cells. The option of a direct determination of the concentration of water vapors in a gaseous mixture is not mentioned, either.

Methods to determine a leakage of fuel gases in a fuel gas system are known from DE 10 2006 001 778 T5 and DE 11 2006 002 060 T5, which are based on estimates and or evaluations of nitrogen concentrations. Both methods are not suitable for the online analysis of fuel cells during operation and omit the use of spectroscopic methods for proof.

SUMMARY

A first aspect relates generally to a method for monitoring and/or regulating fuel cells, by which gaseous components, such as nitrogen or water vapor, can be determined—reliably and with strong proof—online in a fuel cell system as well.

A second aspect relates generally to a method for monitoring and/or regulating fuel cells, comprising determining the composition of operating gases of fuel cells comprising the steps: introducing a gaseous mixture to be analyzed into a measuring cell; creating a light arc in the measuring cell; accepting the radiation emitted by the light arc, optic filtering of the emitted radiation and/or spectral splitting of the emitted radiation; converting the emitted radiation into an electric signal, evaluating the electric signal.

The discharge in the form of a light arc causes the gases to be analyzed to become ionized and the resulting light emissions to be accepted. The light emission of ions can here be used as a specific proof. The generation of ions is useful here, because not all neutral molecules show light emissions that can be utilized.

One embodiment may allow a gaseous mixture to be analyzed reliably and with strong proof For example, slight amounts of nitrogen in the anode exhaust flow in the presence of different concentrations of water vapors can be proven during the operation of a fuel cell and this way the permeability of the membrane can be monitored. Here, leakages in the system can quickly and securely be determined Additionally, this allows a direct control or regulation of the fuel cell processes.

The method may be performed in a particularly cost-effective manner, which is ensured by the simple design of the measuring cell required as well as the low energy consumption.

Further, an efficient and secure monitoring and/or regulation of one or more fuel cells is possible. Here, it may be provided that the emitted radiation is sampled of at least two measuring cells, where the optic filtering of the emitted radiation and/or the spectral analysis of the emitted radiation shall be performed individually for each of the measuring cells or simultaneously. This way, a secure monitoring and/or regulation of stacks of fuel cells is possible, with only a single analysis unit being required.

In one exemplary embodiment of the method, the light arc is generated by applying alternating voltage to electrodes. The alternating voltage at the electrodes has to be sufficiently high and adjusted to the distance of the electrodes in order to achieve the required current density. It is particularly advantageous for the alternating voltage to show a frequency from 20 kHz to 70 kHz. This way it is possible to also ionize molecules, such as water, nitrogen, or hydrogen and this way prove them by spectroscopic methods. The method according to the invention can therefore be used preferably in the atmosphere of a fuel cell. By a more precise selection of the discharge conditions, optimal features of the discharge can be achieved and thus adjusted for the respective analytic objective.

The use of alternating voltage in the frequency range mentioned further offers additional advantages: On the one hand any unilateral electrode incineration is avoided, which might occur in case of direct current arcs and would lead to a geometric displacement of the arc gap and thus a modification of the optic features of the system. On the other hand, the required power sources are easily and cost-effectively available in the market. Here, the use of inverter circuits is particularly advantageous, such as used for example for the operation of cold cathode fluorescent lamps (CCFL). Furthermore, interferences are avoided with radio and mobile phone devices by the use of the above-mentioned frequency ranges. Due to the fact that these inverter circuits already ensure a galvanic separation they also offer the advantage that it is possible to integrate the measuring cell described in the following directly in a stack of fuel cells without any additional isolation measures.

In another advantageous embodiment a voltage is applied to the electrodes ranging from 0.5 kV to 5 kV so that the current developing ranges from 200 µA to 6 mA. This way, the current necessary for the arc discharge and thus the function of the measuring cell is generated. Due to these discharge conditions, optimal features can be achieved for this discharging.

In another advantageous embodiment the emitted radiation is accepted by a light conductor. By the use of a light conductor it is possible to integrate the measuring cell mechanically in a stack of fuel cells or in the housing of a stack of fuel cells, whereas the other components of the analysis equipment may be arranged outside the fuel cell.

A third aspect relates generally to a measuring cell to analyze the composition of the operating gases of fuel cells, comprising a housing, showing a gas inlet and a gas outlet, and a discharge chamber, which is connected to the gas inlet and the gas outlet, with the discharge chamber being at least partially enclosed by the housing and in which an electrode and a counter-electrode are arranged showing an arc gap, with the electrodes being formed to form a light arc and at least one means being provided to accept the emitted radiation.

Such a measuring cell can be produced particularly easily and cost-effectively. Furthermore, the dimensions of such a measuring cell can be kept very small so that measuring cells can be easily integrated in a stack of fuel cells.

In an advantageous embodiment, the electrode and the counter-electrode are embodied in a pin-like fashion with widened or enlarged ends. This way, they show a long life so that any local overheating at the discharge site is avoided, which would lead to a rapid incineration of the electrodes.

In another advantageous embodiment the electrode is embodied as an annular electrode. This way, constructions are possible allowing a more rapid gas exchange in the discharge zone and in which heat released during the discharge is better guided off. By the more rapid gas exchange this embodiment allows a quick detection and thus an efficient regulation of the fuel cell.

In another advantageous embodiment, the housing is embodied in a manner that can be thermostat-controlled. This way, the temperature of the fuel cell can be adjusted, effectively preventing the condensation of water within the measuring cell. This is particularly required when the measuring cell is arranged outside the fuel cell housing or the stack thereof.

In another advantageous embodiment, the means for accepting emitted radiation is embodied as a light conductor. By providing a light conductor it is possible to integrate the measuring cell directly in the housing of a fuel cell or a stack of fuel cells, while the other components of the analysis device can be arranged outside of the fuel cell. This measure is advantageous because no additional thermostat is required to avoid condensation of water in the measuring cell. Furthermore, this way a single optic analysis unit can be used for a multitude of measuring cells. This is particularly advantageous for the fuel cells to be arranged as stacks or several stacks combined to a larger system. The suggested design shows the advantage that it is robust and stable in reference to external influences.

BRIEF DESCRIPTION

Additional advantages and advantageous embodiments are illustrated in the drawings and explained in the following description. Here, it must be considered that the drawings are only of a descriptive character and are not intended to limit the invention in any form.

Figure 4:
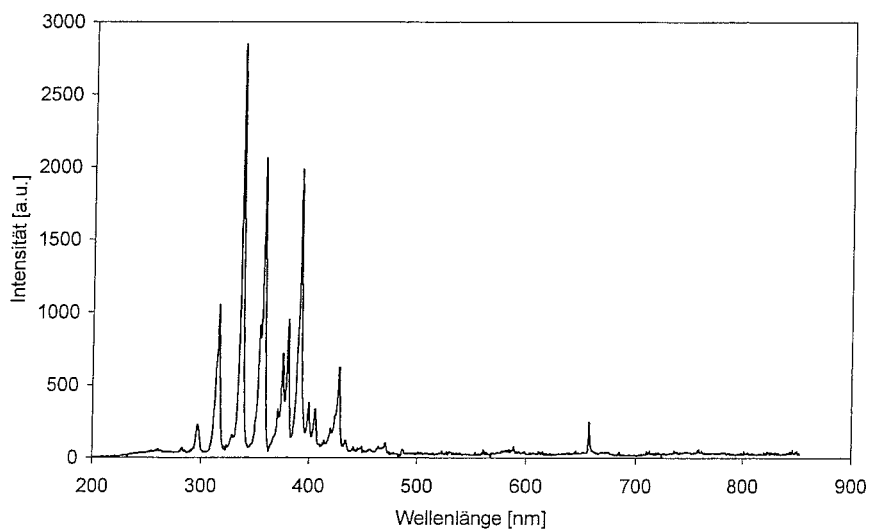
Figure 5:
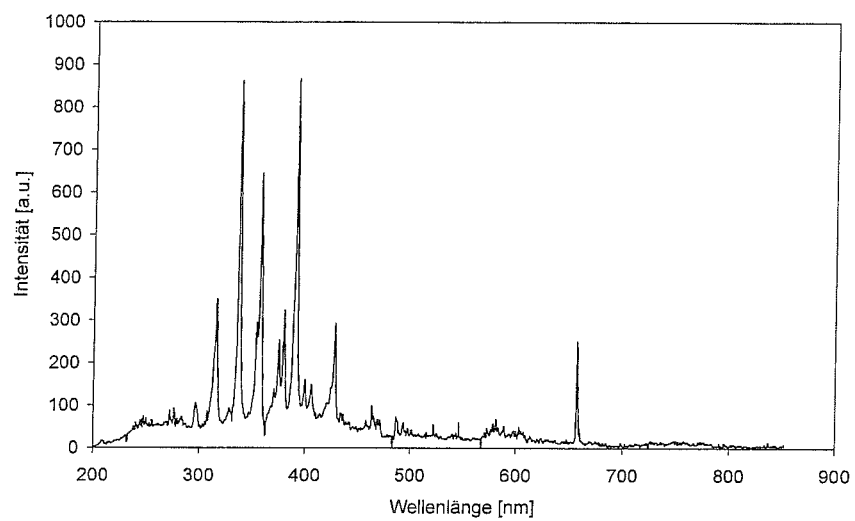
Figure 6:
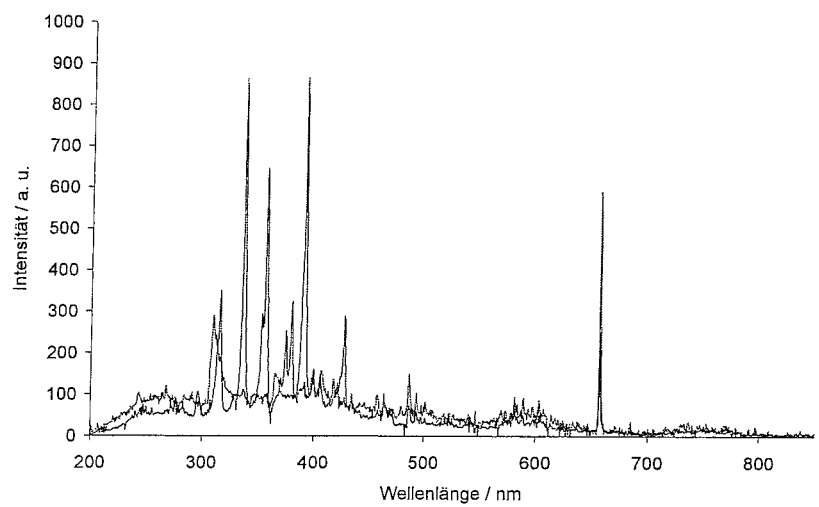
Figure 7:
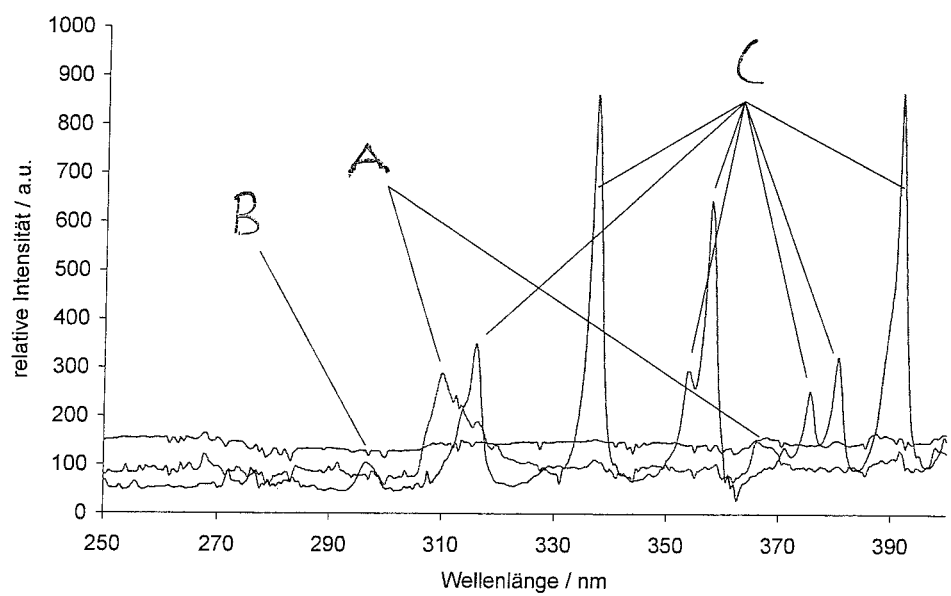
Figure 8:
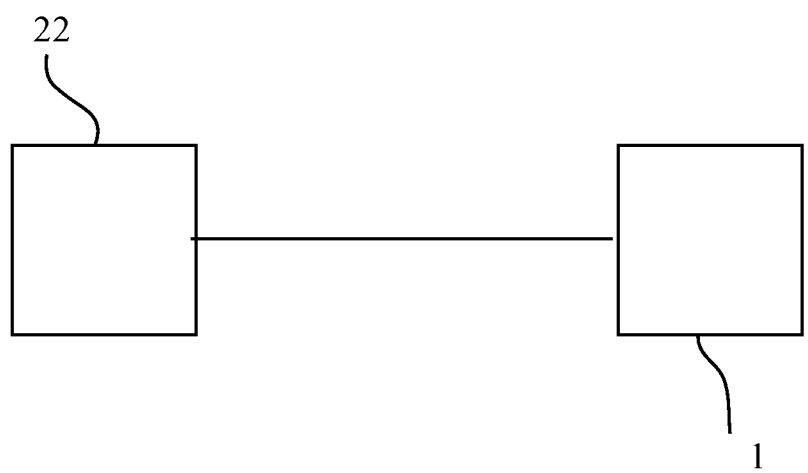

FIG. 4 shows a typical discharge spectrum of a hydrogen/nitrogen mixture in a mixing ratio of 1:1, FIG. 5 shows a typical discharge spectrum of a hydrogen/nitrogen mixture in a mixing ratio of 5:1, FIG. 6 shows a typical discharge spectrum of a water vapor-saturated hydrogen/nitrogen mixture in a mixing ratio of 5:1 and a discharge spectrum of water vapor-saturated pure hydrogen, FIG. 7 shows an enlarged view of the spectrum of FIG. 5A, FIG. 8 shows a schematic view of an embodiment of a measuring cell in fluid communication with a fuel cell.

DETAILED DESCRIPTION

Figure 1:
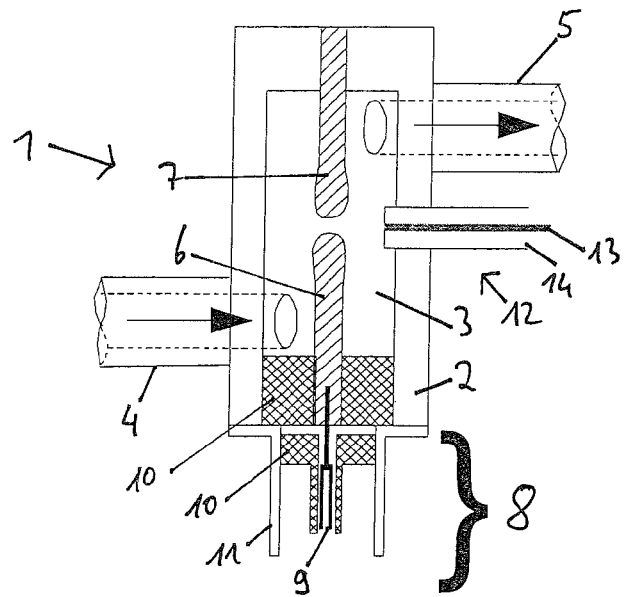
FIG. 1 shows the design of an embodiment of a measuring cell.

FIG. 1 shows a measuring cell 1, embodied for the method according to the invention to monitor and/or regulate fuel cells. Preferably the measuring cell 1 is embodied as a discharge cell and is arranged at the end of the anode gas channel of a fuel cell, such as fuel cell 22, as shown in FIG. 8. The measuring cell 1 may be directly looped into the anode gas channel or connected thereto via a bypass.

According to FIG. 1, the measuring cell 1 comprises a gas-tight housing 2, with its interior forming a discharge chamber 3. The discharge chamber 3 is therefore at least partially encased by the housing 2. The housing 2 further comprises a gas inlet 4 and a gas outlet 5, through which the gas to be measured can be guided into or out of the measuring cell 1. With regards to the connector for the gas inlet 4 and the gas outlet 5, a plug-in system is advantageous, which may be designed in such a way that it is sealed in a gas-tight fashion from the environment. This ensures, if necessary, the ability for quickly exchanging the measuring cell 1. This is particularly advantageous because this way, for example in case of malfunction for example by electrode incineration or entered liquid water, replacement can be ensured quickly.

In the interior chamber of the discharge chamber 3, the electrode 6 and the counter-electrode 7 are arranged such that arc discharge can occur between them. The electrode gap, i.e., the size of the distance between the electrode 6 and the counter-electrode 7 can here be variably adjusted in an advantageous embodiment of the measuring cell. This way, the selection of optimal discharge conditions is possible for proving particular gases. However, this discharge gap is typically formed by a gap of a few 100 μm between the electrode 6 and a counter-electrode 7 suitable for maintaining a light arc.

Preferably the housing 2 is formed partially or entirely from metal. This way, it is easily possible to control the measuring cell 1 via thermostats to the temperature of the fuel cell. This is of great importance for the operation in a combination of a fuel cell and a measuring cell 1 because here the condensation of water can be effectively prevented in the discharge chamber 3. This way it is prevented that condensed water may lead to creeping current or sparks in the measuring cell 1, which might falsify the measuring results or even damage the cell.

The exterior dimensions of the housing 2 are advantageously limited to a few centimeters. The radius of the preferably cylindrical housing 2 may range from 1 to 1.5 cm, and the length of the housing may range from 2 to 3 cm. This way, the measuring cell 1 is very compact and easily suitable for use in fuel cell systems.

In order to generate a light arc, the electrodes 6, 7 may be supplied with an alternating voltage. For this purpose the measuring cell 1 preferably comprises a connection 8 at its electrode 6, which may be embodied as a detachable electric connection. This may be a commercial BNC-connector, for example. When using such a plug-in system the electrode 6 is connected in a conductive fashion to the interior contact spring 9. The electrode 6 is separated from the housing 2 by a gas-tight electric isolator 10, with, in an advantageous embodiment, the exterior contact 11 being electrically connected to the housing 2.

The alternating voltage may be generated by an inverter circuit, converting direct voltage into the required alternating voltage. Such inverter circuits are used, for example, for the operation of cold cathode fluorescent lamps (CCFL), as known among other things for the background illumination of TFT-monitors. Advantageously, here depending on the dimensions of the circuit, alternating voltage is used ranging from 20 to 70 kHz. Further, the voltage emitted preferably amounts to a few kV, particularly the voltage emitted ranges from 0.5 to 5 kV, so that during operation of the measuring cell currents develop from 200 μA to 6 mA. These statements represent values of technical limits, whose range may be used to adjust the method to various cell geometries or other factors. By selecting the values within the above-mentioned limits the required current density is achieved in order to ensure the arc discharge necessary for the function of the measuring cell.

The anode gas of a PEM-fuel cell forms a strongly reduced atmosphere, because primarily hydrogen, water, small amounts of nitrogen, and trace gases are present. In order to be sufficiently constant under these conditions the electrodes 6, 7 may therefore comprise gold or gilded metals.

In an advantageous embodiment a light conductor 12 may be arranged laterally in reference to the electrode gap between the electrodes 6, 7, provided with a standardized connector 14, which can also be sealed air-tight in reference to the environment. Preferably the optic core 13 of the light conductor 12 is made from fiberglass or optic fibers comprising organic polymers. The light conductor 12 serves to accept the light emitted by the gaseous mixture to be measured and to conduct it to a detection system. The advantage of the use of a light conductor 12 is particularly that only one measuring cell 1 is required per se inside the fuel cell system or the stack and a spatial separation of the optic detection system and the gas discharge cell and/or the measuring cell 1 is possible. This way, the option is provided to guide a multitude of light conductors starting at various measuring cells 1 to only a single optic analysis unit, such as an optic dispersion and detection system. The signals of the individual measuring cells may either be optically switched or registered simultaneously.

When a voltage is applied to the electrodes, as described above, a light arc is arranged between the electrodes, exciting the gases included in the gaseous mixture to be examined for specific emissions. By the light conductor 12 the emitted radiation is accepted and preferably conducted to an optic dispersion unit. Here, the emitted radiation is spectrally split-ted. The spectral splitting may occur by transmission or reflection grids, optic film grids, or prisms or prism combinations made from polymer materials or different types of glass. Depending on the detector used, here it is possible to operate the dispersion unit as a spectrometer, i.e., with a mobile dispersion element for a temporal scanning of the spectrum or as a spectrograph, i.e., with a simultaneous recording and further processing of the entire spectrum. Additionally or alternatively it is possible to mask undesired wavelengths of the spectral range by the use of optic filters upstream or downstream in reference to the dispersion unit, thus optically filtering the emitted radiation. For this purpose, color filters, edge filters, interference filters, band-pass filters, or combinations thereof may be used. Furthermore, the radiation must be converted into an electric signal, in order to then be evaluated. Here, in the first case for example photo cells, photo multipliers, or photo diodes can be used to perform the conversion into electric signals, in the second case CMOS or CCD detectors. The assessment of the electric signals may be performed by methods known to one trained in the art, for example gas spectra as shown in the following.

In facilities designed for measuring a single trace gas, the dispersion unit may be waived and replaced by a suitable optic band pass filter, which is advantageously coupled to a photo cell or photo diode as the detector.

In the method it is possible to realize the regulation and/or control of the fuel cell processes directly online using the measuring cell according to the invention. For example, fuel cell processes can be monitored directly at the cell itself and perhaps the operating parameters can be immediately regulated or newly set. Furthermore, the measuring cell can be directly connected to an alarm. This way, when reaching a critical status a warning signal is issued or the fuel cell processes may be stopped, if necessary.

In particular in stacks of fuel cells it is here advantageous when a measuring cell 1 is provided for each fuel cell. However, in order to allow radiation emitted from the measuring cell 1 to be analyzed by only one analysis unit, it is advantageous for the light conductors 12 to be merged upstream in reference to an analysis unit. Here, depending on the evaluation desired, it may be provided that the optic filtering of the radiation emitted and/or the spectral analysis of the emitted radiation is performed individually for each of the measuring cells 1, or simultaneously.

This way, secure monitoring and/or control of stacks of fuel cells are also possible, with only one analysis unit being required, here.

In an advantageous embodiment the measuring cell is located in the outlet of the anode exhaust flow or in a bypass thereof; however, it may also be provided at any arbitrary other position in the anode gas flow of the fuel cell or in another gas flow to be examined.

In order to shield the electric stray field the alternating voltage of the measuring cell is preferably conducted via a coaxial cable. With regards to the supplied alternating voltage, the housing 2 may then be connected to the mass potential or the potential of the anode of the fuel cell or the stack. This way, it is additionally prevented that in case of a leak in the fuel cell system hydrogen can be ignited by sparks between the measuring system and other electrically conductive parts. Further, in an advantageous embodiment heat-conducting diaphragms may be provided in the gas inlet 4 or the gas outlet 5 of the measuring cell 1 each in order to securely prevent the ignition of the oxyhydrogen gas developing in case of air penetrating the anode gas system. Here, particularly copper sieves or interposed bronze frits may be used as heat-conductive diaphragms.

Figure 2:
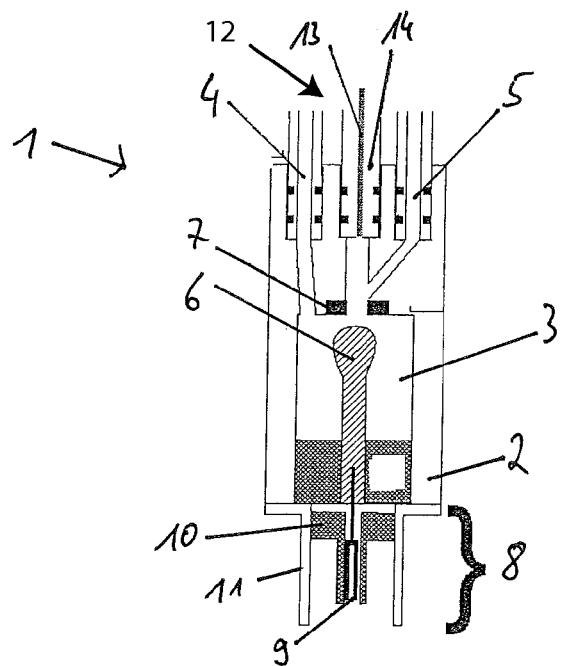
FIG. 2 shows the design of an alternative embodiment of a measuring cell.

FIG. 2 shows another embodiment of a measuring cell. The design is similar to the one in FIG. 1. According to FIG. 2, the measuring cell also shows a gas inlet 4 and a gas outlet 5. Through them the gas to be measured can be guided in or out of the measuring cell 1. According to FIG. 2 the measuring cell comprises an electrode 6, which may be formed similar to the electrode in FIG. 1; however, here it is provided that the counter-electrode 7 is embodied as an annular electrode. In this form it can be embodied as a part of the housing 2.

Furthermore, an embodiment of the measuring cell according to FIG. 2 also comprises a connection 8, particularly a plug-in connection, such as a BNC-connector. This way, the voltage can be applied to the electrode, as explained in reference to FIG. 1, in order to generate an arc discharge. A light conductor 12 is provided to conduct the radiation generated in this way to the dispersion and detection system, thus a spectrograph, for example. However, according to FIG. 2, it may also be arranged like the electrode 6 in the geometric axis of the annular electrode. This allows in an advantageous embodiment of the measuring cell for better protection of the inlet of the light conductor 12 from contaminants. Contaminants may develop by material sputtered off the electrodes. The gas inlet 5 is arranged in reference to the light conductor such that by the direction of gas flow the contaminants are kept away from the light conductor. Further, contrary to the above-mentioned, by this design a more rapid gas flow is possible in the discharge zone and thus the fuel cells become faster and accordingly more efficient.

When the method is performed, here the gaseous composition can be examined in the anode chamber of the fuel cell. Typically developing spectra are shown in the following figures.

The spectral emission of molecular nitrogen here shows a characteristic band pattern in the near ultraviolet range, which is clearly distinguished from the weak continuous emissions of molecular hydrogen in this spectral range. When molecules present in the discharge chamber 3 are electrically excited in a light arc, molecular nitrogen, for example, can be proven based on the emission spectra developing in the gaseous mixture up to a very high dilution.

Figure 3:
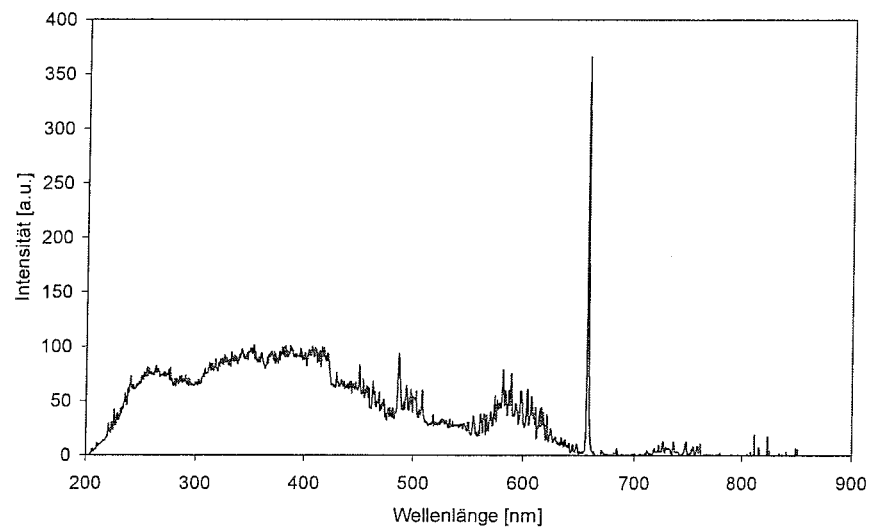
FIG. 3 shows a typical discharge spectrum of pure hydrogen.

FIG. 3 shows a typical spectrum of an arc discharge in a pure hydrogen atmosphere. The hydrogen spectrum covers the spectral range from 200 to 650 nm under the conditions selected (temperature 298 K, pressure approximately 1000 hPa, flow rate 60 standard milliliters per minute) of the electric discharge only from wider transfers with a low intensity. Only the sharp line at 656.8 nm (the so-called $H_\alpha$ line) is striking in the spectrum of hydrogen. In such a spectrum the spectral lines of nitrogen are easily discernible, as shown in FIG. 4.

FIG. 4 shows a discharge spectrum of a 1:1 mixture of hydrogen and nitrogen recorded under the same conditions as the one shown in FIG. 3. Here, particularly in the spectral range from approximately 300 to 450 nm the bands of the nitrogen discharge are easily discernible, which show high intensity. This is particularly discernible from the ratio of the intensity of the hydrogen line at 656.8 nm compared to the nitrogen bands.

As shown in FIG. 5, in a hydrogen-nitrogen atmosphere with a mixing ratio of 5:1 the bands of nitrogen are clearly discernible in reference to the underlying signals of hydrogen. It is discernible from FIG. 5 that nitrogen can still be easily detected even in a clear excessive amount of hydrogen. A detection threshold for nitrogen of less than one percent by volume can be achieved here.

In addition to the clear proof of nitrogen in the presence of even severely excessive hydrogen, it is further important that even in the presence of water vapors the proof of nitrogen is not compromised, but it can also be quantified even in addition thereto or independently therefrom by the method described. Water is always present in polymer membranes or must be supplied to the fuel cell by an external moistening of the gas supply in order to ensure the charge transport in the membrane. A spectrum of a gaseous mixture comprising hydrogen and nitrogen at a ratio of 5:1 and saturated with water vapor is shown in FIG. 6. FIG. 7 shows an enlarged detail of the spectrum of FIG. 6 at the range from 250 to approximately 400 nm. In the conditions selected the spectrum shows a distinct water signal of approximately 310 nm (curve A), as clearly discernible from FIG. 7. This shows that the detection of hydrogen (curve B) and nitrogen (curve C) is possible when simultaneously water vapors are present. This is also discernible in FIG. 6, where a spectrum of hydrogen saturated with water vapors and a hydrogen/nitrogen mixture (5:1) saturated with water vapors are superimposed.

The invention claimed is:

1. A method for monitoring fuel cells to determine a permeability of one or more electrolyte membranes in the fuel cells, the method comprising:
    determining a composition of one or more operating gases of the fuel cells, wherein the composition is analyzed for an amount of nitrogen and wherein the amount of nitrogen in the composition of one or more operating gases indicates a level of permeability of the one or more electrolyte membranes, further wherein the step of determining the composition of the one or more operating gases includes the steps:
        introducing a gaseous mixture to be analyzed into a measuring cell, the measuring cell being located in at least one of an outlet of an anode exhaust flow of a fuel cell and a bypass thereof;
        creating a light arc in the measuring cell;
        accepting a radiation emitted by the light arc;
        performing at least one of optically filtering of the emitted radiation and spectral splitting of the emitted radiation;
        converting the emitted radiation into an electric signal; and
        evaluating the electric signal.

2. A method according to claim 1, wherein the light arc is generated by applying an alternating voltage to an electrode and a counter-electrode.

3. A method according to claim 2, wherein the alternating voltage shows a frequency ranging from 20 kHz to 70 kHz.

4. A method according to claim 2, wherein a voltage is applied to the electrode and the counter-electrode plurality of electrodes ranging from 0.5 kV to 5 kV, so that currents develop ranging from 200 µA to 6 mA.

5. A method according to claim 1, wherein the radiation emitted is accepted by a light conductor.

6. A method according to claim 1, wherein the radiation emitted is accepted by at least two measuring cells, with the optic filtering of the emitted radiation being performed individually for each of the measuring cells.

7. A method according to claim 1, wherein the emitted radiation is accepted by at least two measuring cells, with the optic filtering for emitted radiation for each of the measuring cells being performed simultaneously.

8. A method according to claim 1, wherein the radiation emitted is accepted by at least two measuring cells, with the spectral splitting of the emitted radiation being performed individually for each of the measuring cells.

9. A method according to claim 1, wherein the emitted radiation is accepted by at least two measuring cells, with the spectral splitting of the emitted radiation for each of the measuring cells being performed simultaneously.

10. The method of claim 1, wherein the composition is analyzed for an amount of at least two of nitrogen, hydrogen, and water vapor determined next to each other and wherein the amount of the at least two of nitrogen, hydrogen, and water vapor determined next to each other indicates a level of permeability of the one or more electrolyte membranes.

11. A fuel cell system including a measuring cell to analyze a composition of one or more operating gases of fuel cells and to thereby detect a permeability of one or more electrolyte membranes of the fuel cells, comprising:
a housing, showing a gas inlet and a gas outlet; and
a discharge chamber, which is connected to the gas inlet and the gas outlet, with the discharge chamber being enclosed by the housing at least partially and in which an electrode and a counter-electrode are arranged with a discharge gap;
wherein the electrode and the counter-electrode are configured to form a light arc and at least one means being provided to accept an emitted radiation;
wherein the measuring cell is located downstream of an exhaust gas stream of the fuel cells, the exhaust gas stream containing the one or more operating gases of the fuel cells to be analyzed and monitored by the measuring cell;
wherein the measuring cell analyzes the exhaust gas stream containing the one or more operating gases of the fuel cells to detect an amount of nitrogen;
wherein the detection of an amount of nitrogen in the one or more operating gases in the exhaust gas stream of the fuel cells indicates a level of permeability of the one or more electrolyte membranes.

12. A measuring cell according to claim 11, wherein the electrode and the counter-electrode are pin-shaped with enlarged ends.

13. A measuring cell according to claim 11, wherein the electrode is embodied as an annular electrode.

14. A measuring cell according to claim 11, wherein the housing is configured to allow thermostat control.

15. A measuring cell according to claim 11, wherein the means for accepting the emitted radiation are a plurality of light conductors.

16. The system of claim 11, wherein the measuring cell analyzes the exhaust gas stream containing the one or more operating gases of the fuel cells to determine an amount of at least two of nitrogen, hydrogen, and water vapor next to each other; wherein the determination of the amount of at least two of nitrogen, hydrogen, and water vapor next to each other in the one or more operating gases in the exhaust gas stream of the fuel cells indicates the level of permeability of the one or more electrolyte membranes.

17. A measuring cell to analyze a composition of one or more operating gases of fuel cells in order to determine a level of permeability of one or more electrolyte membranes in the fuel cells, comprising:
a discharge chamber having a gas inlet for receiving a sample gas from an anode gas channel of a fuel cell, and a gas outlet, wherein the discharge chamber is enclosed by a housing at least partially;
an electrode and a counter-electrode disposed within the discharge chamber, the electrode and the counter-electrode separated by a discharge gap, the electrode and the counter-electrode being configured to form a light arc within the discharge chamber; and
a light conductor arranged laterally with respect to the discharge gap for accepting emitted radiation;
wherein the sample gas comes directly into contact with the light arc in the discharge chamber;
wherein the measuring cell analyzes the composition of the sample gas to detect an amount of nitrogen as the sample gas exits the fuel cells;
wherein the detection of an amount of nitrogen indicates a level of permeability of the one or more electrolyte membranes in the fuel cells.

18. The measuring cell according to claim 17, wherein the electrode and the counter-electrode are pin-shaped with enlarged ends.

19. The measuring cell according to claim 17, wherein at least one of the electrode and the counter-electrode is an annular electrode.

20. The measuring cell according to claim 17, wherein the housing is configured to allow thermostat control.

21. The measuring cell according to claim 17, wherein the measuring cell analyzes the sample gas to determine an amount of at least two of nitrogen, hydrogen, and water vapor next to each other as the sample gas exits the fuel cells, wherein the determination of an amount of the at least two of nitrogen, hydrogen, and water vapor determined next to each other indicates a level of permeability of the one or more electrolyte membranes in the fuel cells.

* * * * *

UNITED STATES PATENT AND TRADEMARK OFFICE
CERTIFICATE OF CORRECTION

PATENT NO. : 9,030,665 B2  
APPLICATION NO. : 13/512602  
DATED : May 12, 2015  
INVENTOR(S) : Betterman et al.

It is certified that error appears in the above-identified patent and that said Letters Patent is hereby corrected as shown below:

In the specification

Column 4, Line 44, delete "FIG. 5A" and insert -- FIG. 5 --

Signed and Sealed this  
Twelfth Day of January, 2016

Michelle K. Lee  
*Director of the United States Patent and Trademark Office*